United States Patent
Collura et al.

(10) Patent No.: US 7,150,715 B2
(45) Date of Patent: Dec. 19, 2006

(54) NETWORK ENABLED BIOFEEDBACK ADMINISTRATION

(76) Inventors: Thomas F. Collura, P.O. Box 24450, Mayfield Heights, OH (US) 44124; Theresia Mrklas, 715 High St., Bedford, OH (US) 44146

(*) Notice: Subject to any disclaimer, the term of this patent is extended or adjusted under 35 U.S.C. 154(b) by 922 days.

(21) Appl. No.: 09/777,107

(22) Filed: Feb. 5, 2001

(65) Prior Publication Data

US 2002/0107454 A1    Aug. 8, 2002

(51) Int. Cl.
*A61B 5/00* (2006.01)
*A61B 5/04* (2006.01)

(52) U.S. Cl. .................. 600/300; 128/905; 600/545; 600/546

(58) Field of Classification Search .............. 600/545, 600/300 X, 301, 546; 128/904, 905 X, 920; 705/2
See application file for complete search history.

(56) References Cited

U.S. PATENT DOCUMENTS

| | | | | |
|---|---|---|---|---|
| 4,110,918 A | * | 9/1978 | James et al. ............... 434/262 |
| 5,694,939 A | * | 12/1997 | Cowings ................... 600/484 |
| 6,368,268 B1 | * | 4/2002 | Sandvick et al. ........... 600/38 |
| 6,394,904 B1 | * | 5/2002 | Stalker ...................... 463/23 |
| 6,605,038 B1 | * | 8/2003 | Teller et al. ............... 600/300 |
| 2002/0021283 A1 | * | 2/2002 | Rosenberg et al. ......... 345/156 |

* cited by examiner

*Primary Examiner*—Max F. Hindenburg
*Assistant Examiner*—Jonathan Foreman

(57) ABSTRACT

An apparatus and method for controlling a biofeedback session. The system utilizes distributed processing that includes localized processing capability allowing a user to initiate a self-controlled biofeedback session and additionally includes remote processing capabilities enabling simultaneous remote analysis and monitoring of the session.

10 Claims, 4 Drawing Sheets

NETWORK ENABLED BIOFEEDBACK ADMINISTRATION

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A "MICROFICHE APPENDIX"

Not applicable.

BACKGROUND OF THE INVENTION

1 Field of the Invention

The present invention pertains generally to EEG biofeedback for learning and controlling bio-electric characteristics of the brain which correspond to different mind states and more particularly to an apparatus and method for reducing stress in a human subject through the production of soothing audio, visual and other sensory effects that is capable of being monitored or modified at a remote location.

2 Description of the Related Art Including Information Disclosed Under 37 CFR 1.97 and 37 CFR 1.98.

EEG (brainwave) signals have been extensively studied in an effort to determine relationships between frequencies of electrical activity or neural discharge patterns of the brain and corresponding mental, emotional or cognitive states. Biofeedback of identified frequency bands of EEG signals is used to enable a person to voluntarily reach or maintain a target mental state.

Frequency bands of EEG readings used in such biofeedback have been generally categorized in the approximate frequency ranges of:

delta waves, 0 to 4 Hz;
theta waves, 4 to 7 Hz;
alpha waves, 8 to 12 Hz;
beta waves, 12 Hz to 36 Hz, and
sensorimotor rhythm (SMR) waves, 12 to 15 Hz.

It is theorized that each of the major subbands of biofeedback EEG (delta, theta, alpha, beta) has unique bioelectric characteristics which correspond with unique subjective characteristics of an individual. The delta band is observed most clearly in coma and deep sleep, the theta band in light sleep and drowsiness, the alpha band in a variety of wakeful states involving creativity, calm and inner awareness, and the beta band in alert wakeful situations with external focus. In general, a dominant brain wave frequency increases with increasing mental activity.

Biofeedback systems are well known in the art for use in detecting levels of stress in subjects and providing the appropriate stimuli to affect and alter the flow of brain wave patterns The biofeedback system monitors and processes bioelectrical signals generated in specific topological regions of a subject's nervous system and produces a sensory stimulus if the system detects the presence or absence of certain characteristics in the signal's wave form patterns. These characteristics maybe correlated with a certain desired condition of the subject's nervous system. The sensory stimulus provided by the biofeedback system, typically an audio or visual stimulus, or combination thereof, is fed back to the subject which associates the presence of the stimulus with the goal of achieving the desired condition of its nervous system. By responding to the stimulus, the subject can be trained to control the waveform patterns of the monitored bioelectrical signals and thereby control his or her own nervous system. Such a system is illustrated in U.S. Pat. No. 3,727,616 to Ross.

Many different approaches have been taken to EEG biofeedback to achieve mental state control. U.S. Pat. No. 4,928,704 describes a biofeedback method and system for training a person to develop useful degrees of voluntary control of EEG activity. EEG sensors are attached to cortical sites on the head for sensing EEG signals in a controlled environmental chamber. The signals are amplified and filtered in accordance with strict criteria for processing within time constraints matching natural neurologic activity. The signals are filtered in the pre-defined sub-bands of alpha, theta, beta and delta, and fed back to the monitored person in the form of optical, aural or tactile stimuli.

Because biofeedback devices operate on the basis of internal stimuli, that is, stimuli produced in response to bioelectrical signals generated by the subject, the success of the true biofeedback device is dependent upon a subject attempting to consciously control his or her state of stress. Many people cannot effect such control over their involuntary nervous systems.

U.S. Pat. No. 5,304,112 to Mrklas et al. and U.S. Pat. No. 5,899,867 to Collura, both of which are incorporated herein by reference, each disclose a standalone, computerized system wherein a single user's mental activity is monitored by a computer which provides feedback to the user corresponding to the monitored mental activity. In addition to the user using the equipment, a monitor such as a therapist or health care provider may also be present. A limitation of these systems is that all communications and control functions are located in a single microprocessor and the user, monitor and all data acquisition and computing equipment must be in the same proximity, and can not be spatially separated. Additionally, all data and resources available to the diagnostic, therapeutic, and training systems must also be located in close proximity to the system. It is necessary to deploy hardware and software in such a manner that complete autonomous offices are established. Presently, there is no capability to distribute processing, control, resources, or expertise between or among the various systems.

A drawback to the current systems is that a professional desirous of monitoring a session must travel to the user's location, or the user must travel to the professional's location. This may not always be convenient, practical, or even possible. Thus, the current systems are limited in the availability of training and services available.

Therefore, the need exists for a system which can facilitate distribution of functions and services to local and remote locations in such a manner that an expert diagnostic and therapeutic practitioner can administer care to an individual user from a remote location. Data which may be transmitted to the remote location includes, but is not limited to medical monitoring devices, biofeedback and neurofeedback devices, blood pressure, bio-electric devices, heart monitors, and medication dispensers and pumps.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of instrumentalities and combinations particularly pointed out in the appended claims.

BRIEF SUMMARY OF THE INVENTION

In view of the aforementioned needs, the invention contemplates a system that distributes functions and services in such a manner that an expert diagnostic and therapeutic practitioner can monitor and administer a user's session from a remote location while the user simultaneously receives instant feedback from computerized diagnostic and therapeutic equipment at the user's location.

Input means receives data from the user. The input means may be comprised of video, audio, or physiological sensors. Many physiological sensors are common in biofeedback applications, including but not limited to an encephalograph that that measures electrical potentials on the scalp and generates a record of the electrical activity of the brain ("EEG"); a cardiograph which is used in the detection and diagnosis of heart abnormalities that measures electrical potentials on the body surface and generates a record of the electrical currents associated with heart muscle activity ("EKG"); an electromyograph ("EMG") that senses the electrical activity of a muscle and optionally makes a graphic record; or a galvanic skin response meter that measures galvanic skins response ("GSR") that is a change in the ability of the skin to conduct electricity, caused by an emotional stimulus, such as fright. Furthermore, the input means may be comprised of a combination of video, audio, and physiological sensors.

The user receives output from a feedback means which can expose the user to a plurality of sensory phenomena. Similar to the input means, the typical feedback means outputs video, audio, or physiological stimulation. For video feedback, often a light pattern is displayed on a monitor or television screen wherein the shape of the pattern or intensity of the light is varied. For audio stimulation, speakers or headphones may be used to projecting various sounds or music. Electrical stimulation, tactile stimulation such as vibration or pressure, thermal stimulation, or olfactory stimulation also may be used for providing physiological feedback. The various methods of providing feedback may be used alone or in any combination thereof.

A local computer is connected between the input means and feedback means. The local computer receives the input from the input means, process the data and produces an output which is sent to the feedback means. Additionally, the user may be provided with controls at the local computer to adjust the feedback.

A remote computer is connected to the local computer, providing additional control and analysis of the biofeedback session from a remote location. The remote computer would be connected to the local computer over either a wired or wireless network. In the preferred embodiment, the Internet would be utilized for communications between the remote and local computers. The remote computer would be capable of outputting session information to a monitor at the remote location. The session information could be either the input data being received by the input means, the output being produced by the local computer, or a combination of both. Optionally, the monitor can select which session parameters are output. For example physiological data may be displayed on a monitor, alternatively a video of the session may be played simultaneously with the physiological data, and audio of the session may also be output. The remote computer would have means connected to it for receiving input from the monitor, enabling the monitor to adjust the parameters of the session. The remote computer would communicate the input from the monitor to the local computer which could then adjust output being sent to the feedback or modify or change the input parameters being input into the system.

Additionally, the remote means has additional software for monitoring the session. The remote software may perform more intense computations or process long term trends. Based on the results of the computations, the software on the remote computer can adjust session parameters, such as the output from the local computer.

By utilizing a combination of remote software and remote input and output means, a single monitor may simultaneously monitor a plurality of sessions. This could enable a group session. Optionally, the monitor may select certain parameters causing the remote software to activate an alarm based on specified parameters.

In an alternative embodiment, the remote processor only has one feedback loop. This feedback loop, comprised of software only would perform long term trending an analysis. This would enable biofeedback session to occur when no monitor is available. This could also enable a plurality of local computers to communicate to a single remote computer, wherein the remote computer would contain more sophisticated software for more intensive data analysis which may be performed either real time or in a batch mode of operation. The remote computer, after performing the additional calculations or analysis, could then adjust session parameters for a particular user. Additionally, a database at the remote computer may be utilized to store session information and various parameters changes which can be reviewed by a professional at a later time.

In yet another embodiment of the invention, the remote computer would be capable of remote outputting of session data and remote inputting of system parameter changes by the monitor. In this embodiment, only the monitor would adjust the system parameters from the remote location. This embodiment may be useful for short term group therapy sessions where long term trending an analysis is not necessary. This embodiment is also useful where a professional wishes to monitor a user from a long distance, but does not desire to spend the extra costs for additional computing resources.

In still yet another embodiment of the present invention, a user would utilize a local computer connected to the input means and feedback means, a first remote computer, and a second remote computer. The three computers would be interconnected either by a wired or wireless network, preferably the Internet. The first remote computer having software for monitoring a biofeedback session and capable of adjusting the output of the local computer, and ultimately the feedback received by the user. The second remote computer having remote input means and remote output means enabling a monitor from a location spatially separated from the local computer and first remote computer to observe the session and make adjustments. Optionally, the second remote computer would have additional software for analyzing and adjusting the local computer output. This embodiment would be useful in a case where a health care provider desires utilize a plurality of local computers for biofeedback sessions and a plurality of monitors for monitoring the sessions. By utilizing this arrangement, one monitor may be able to consult with a second monitor who can also analyze and control the biofeedback session. Furthermore, the health care provider can make either global changes to all of the local computers or incremental changes to a particular session from the first remote computer.

The present invention also contemplates a method for controlling a biofeedback session utilizing a distributed biofeedback system. The process begins by receiving data from a user. The data may be video, audio, or physiological. This data is then processed at a local computer which produces a local feedback output based on the data. The data is also sent to another computer at a remote location. Further analysis of the data is performed at the remote location. Based on analysis of the data at the remote location, the local feedback output at the local computer can be adjusted. The feedback is then communicated to the user.

Among those benefits and improvements that have been disclosed, other objects and advantages of this invention will become apparent from the following description taken in conjunction with the accompanying drawings. The drawings constitute a part of this specification and include exemplary embodiments of the present invention and illustrate various objects and features thereof.

BRIEF DESCRIPTION OF THE SEVERAL VIEWS OF THE DRAWING

The drawings illustrate the best mode presently contemplated of carrying out the invention.

The drawings.

DETAILED DESCRIPTION OF INVENTION

Figure 1:
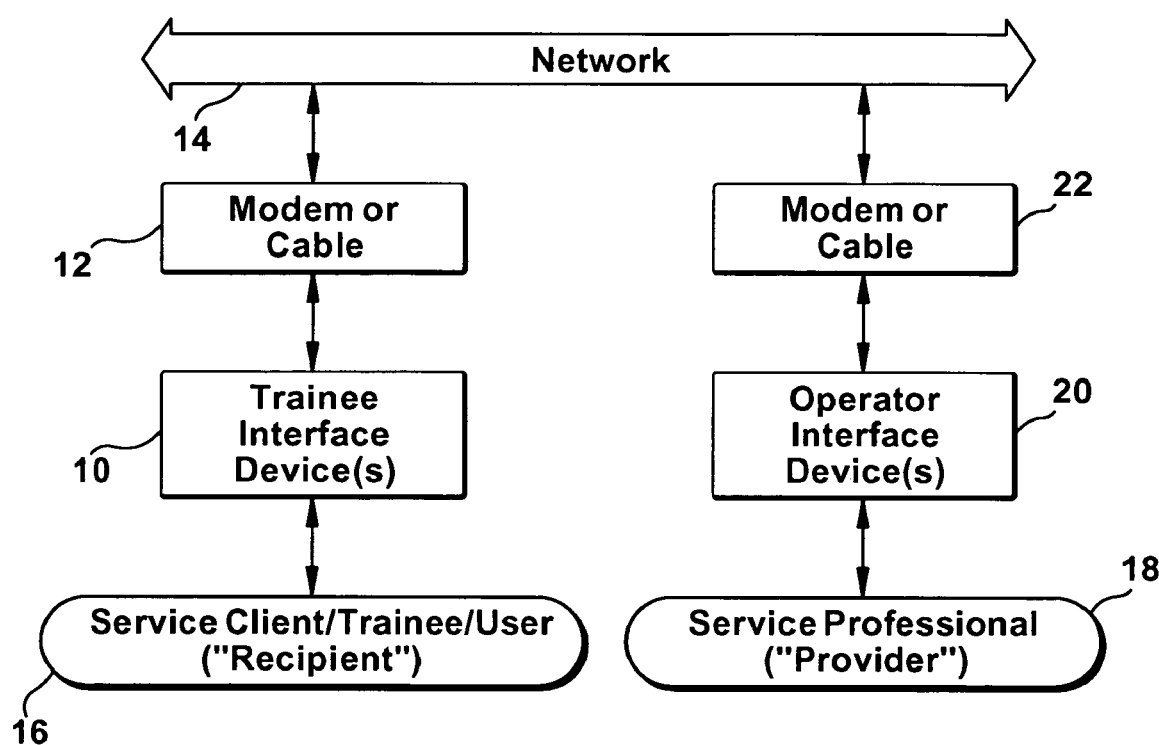
FIG. 1 is a schematic representation of the hardware components of the system of the present invention.

With reference to FIG. 1, there is illustrated the basic components necessary for a biofeedback session utilizing the system of the present invention. The system includes a user interface device 10. The user interface device 10 is comprised of various components for receiving input from a user 16, a processor ("local processor") for processing the input and producing an output which is received by the user 16. The user interface device 10 has communications means 12, usually either a modem or network interface card for connecting to a network 14. The typical connection between the communications means 12 and the network 14 would include cabling, however, in the case of wireless networks the connection may be made by radio or optical waves.

Similarly, at a remote location is a remote interface device 20. The remote interface device 20 has means which allows a service professional or session monitor 18 to monitor the biofeedback session. The remote interface device 20 is comprised of various components for outputting data received by the user interface device 10 to the session monitor 18, and for receiving input from the session monitor 18. The remote interface device 20 has communications means 22, usually either a modem or network interface card for connecting to a network 14. The typical connection between the communications means 22 and the network 14 would include cabling, however, in the case of wireless networks the connection may be made by radio or optical waves with the appropriate transceivers located at the communications means 12 and the network 14.

The network 14 connecting the user interface device 10 to the remote interface device 20 may be comprised of a plurality of local area networks and in the preferred embodiment would utilize the Internet. By utilizing the Internet, the user interface device 10 and the remote interface device 20 may be spatially segregated by hundreds or thousands of miles.

Figure 2:
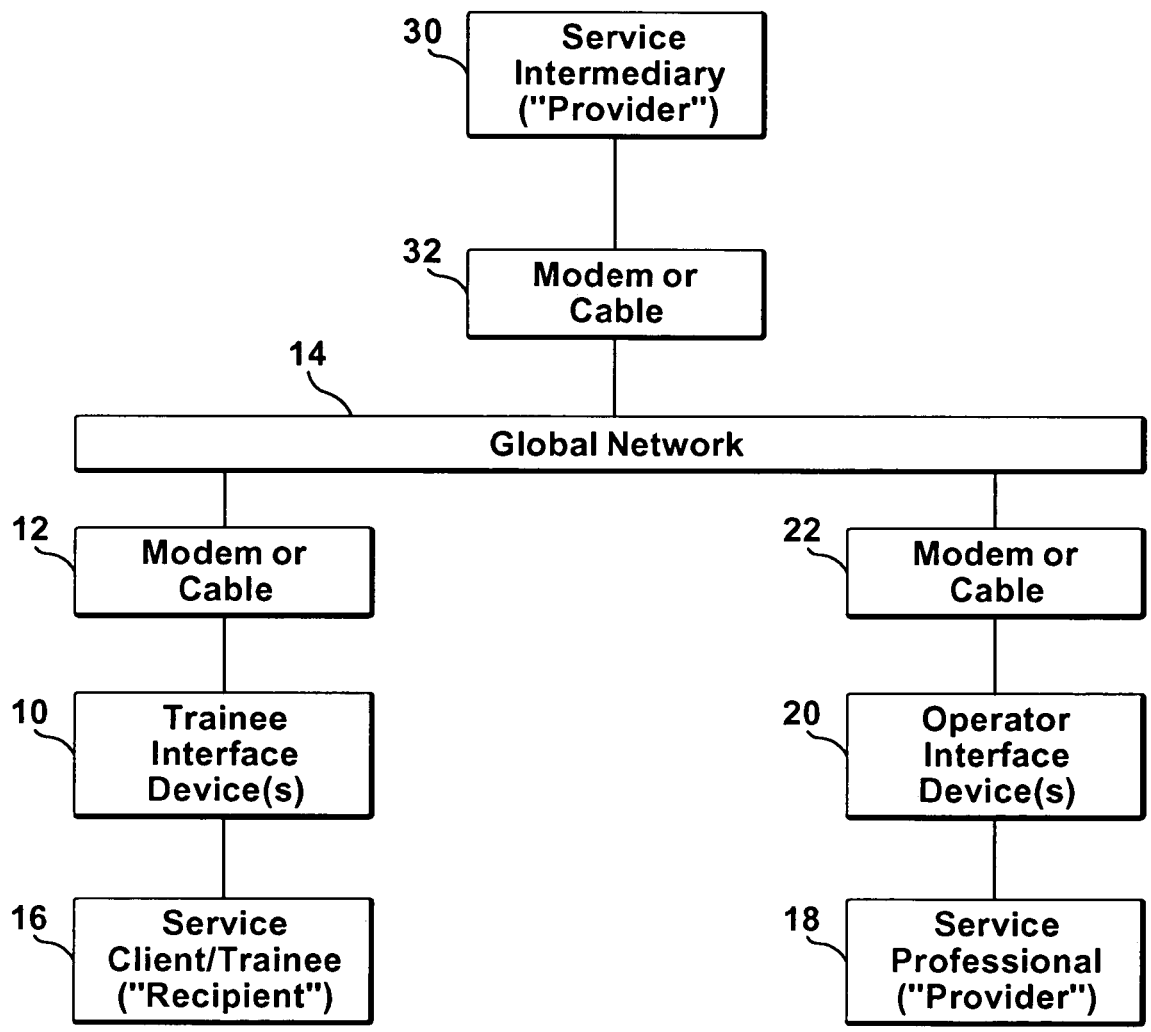
FIG. 2 is a schematic representation of the hardware components of an alternative embodiment of the system of the present invention.

With reference to FIG. 2 is shown an alternative embodiment of the present invention. This embodiment includes the addition of a secondary remote device 30. The secondary remote device 30 is also connected to the network 14 by communications means 32, usually either a modem or network interface card for connecting to a network 14. Similarly, the typical connection between the communications means 32 and the network 14 would include cabling or in the case of wireless networks the connection may be made by radio or optical waves. As will be described further, the secondary remote device 30 also receives all results from the user interface device 10. The secondary remote device 30 can provide additional monitoring or diagnostics of the biofeedback session.

Figure 3:
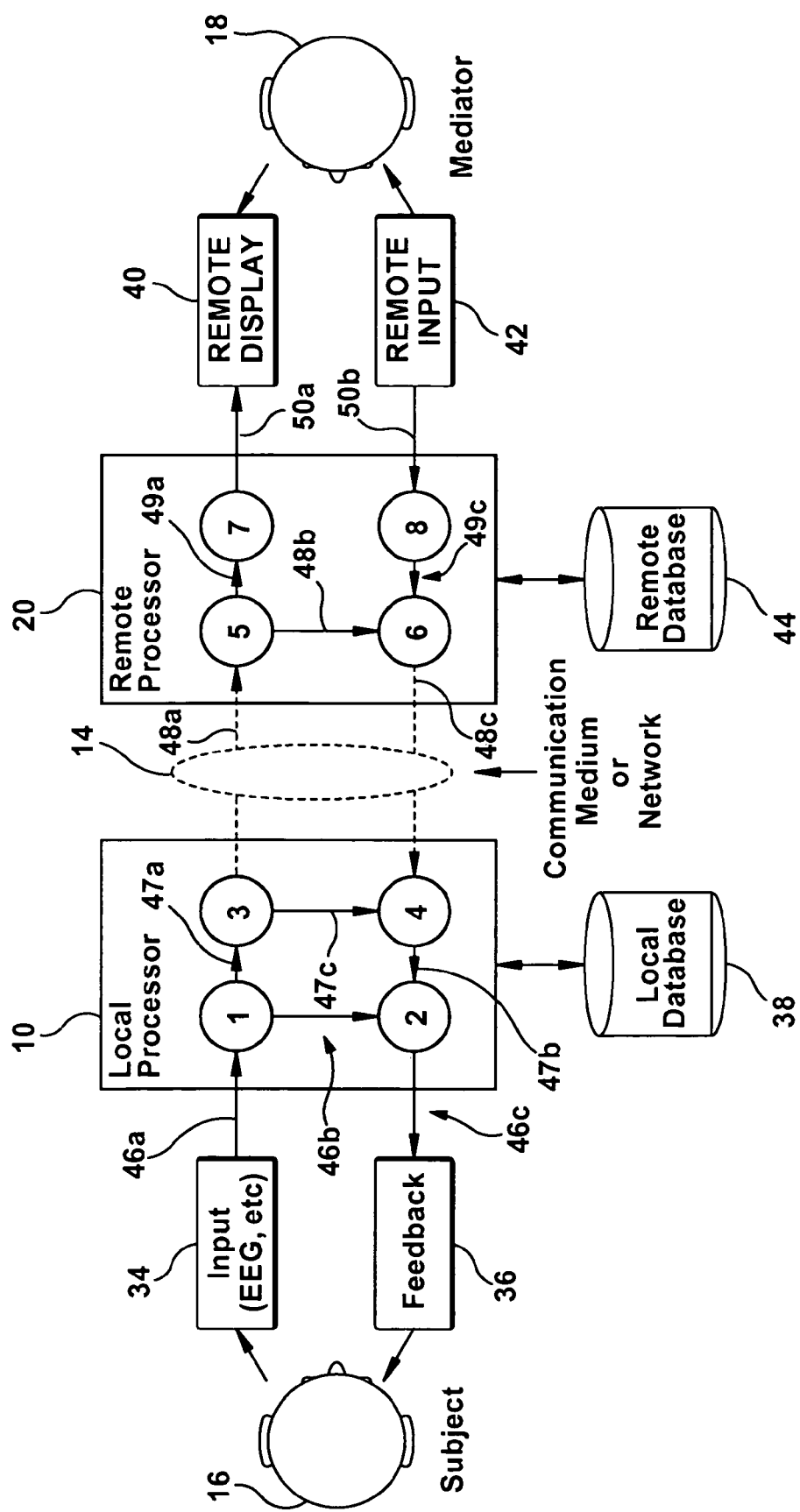
FIG. 3 is a detailed block diagram of the hardware components of the present invention.

Now referring to FIG. 3, a more detailed description of the various hardware components of the present invention are illustrated. A user 16 is connected to a user interface device 10 through the input means 34 and the feedback means 36. Once the user is connected to the input means 34 and feedback means 36, a biofeedback session is initiated. The input means 34 connected to the user 16 may be comprised of video, audio, or physiological sensors. Many physiological sensors are common in biofeedback applications, including but not limited to an encephalograph that that measures electrical potentials on the scalp and generates a record of the electrical activity of the brain ("EEG"); a cardiograph which is used in the detection and diagnosis of heart abnormalities that measures electrical potentials on the body surface and generates a record of the electrical currents associated with heart muscle activity ("EKG"); an electromyograph ("EMG") that senses the electrical activity of a muscle and optionally makes a graphic record; or a galvanic skin response meter that measures galvanic skins response ("GSR") that is a change in the ability of the skin to conduct electricity, caused by an emotional stimulus, such as fright. Furthermore, the input means may be comprised of a combination of video, audio, and physiological sensors.

The user 16 receives output from a feedback means 36 which can expose the user to a plurality of sensory phenomena. Similar to the input means, the typical feedback means outputs video, audio, or physiological stimulation. For video feedback, often a light pattern is displayed on a monitor or television screen wherein the shape of the pattern or intensity of the light is varied. For audio stimulation, speakers or headphones may be used to projecting various sounds or music. Electrical stimulation, tactile stimulation such as vibration or pressure, thermal stimulation, or olfactory stimulation may also be used for providing physiological feedback. The various methods of providing feedback may be used alone or in any combination thereof.

The user interface device 10 is comprised of a computer processor with a plurality of processing nodes. This processor is local to the user and is often referred to as the local processor. The processing nodes provide specific processing capabilities. The user interface device 10 also has a local database 38 for storage and retrieval of data received or output from the various nodes and is connected to the network 14 for communications with the remote processor.

The input node 1 of the user interface device 10 receives the data from the input means 34. The input node performs the functions of data acquisition, antialiasing, scaling and shifting of the data received, and artifact rejection. For example, a typical situation for artifact rejection is where an evoked neural response is contaminated by occasional bursts of muscle activity when the subject fidgets.

A primary feedback node 2 of the user interface device 10 produces an output suitable to control the feedback means 36 based on its inputs. The output is communicated to the feedback means 36. One of the inputs 46b to the primary feedback node 2 is from the input node 1. This enables the user 16 to receive physiological data in a simple, direct manner via the feedback means 36. For example, EKG, EEG or heartbeat readings may be displayed on a computer display terminal without any data analysis being performed. Other outputs which may be produced by the primary feedback node 2 include, but are not limited to, pitch and amplitude of sounds; motion, size and shapes of displays; progress of animation; presence of objects; and/or attributes of objects.

The user interface device 10 also has a first-level data node 3. The first-level data node is receives data from the primary input node 1 and performs some data manipulation. Some of the functions which may be performed by the first-level data node 3 are generation of fast fourier transforms or other spectral analysis; digital filtering; artifact rejection; signal averaging; coherence and phase measurement; and computation of derived quantities such as rations, proportions and durations. The first-level data node 3 also prepares and sends data packets over the network 14 to the remote interface device 20.

The first-level feedback node 4 provides for more complex feedback being received by the user 16. The first-level feedback node 4 receives data from the first-level data node as well from the remote interface device 20. The first-level feedback node 4 provides decisions based on threshold settings, decisions based on protocol settings, decisions based on timing and duration of signal parameters and produces outputs providing scaling, and amplitude information as well as decisions for display attributes. In addition, the output of the first-level feedback node 4 may be controlled by the remote interface device 20.

The remote interface device 20 is connected across the network 14 to the user interface device 10. The remote interface device 20 also has a computer processor, that has a plurality of processing nodes. Because this processor is located at a location remote from the user 16, it is often referred to as a remote processor. The remote interface device 20 has a remote database 44 for storage and retrieval of data received or sent from the remote interface device 20.

The remote data node 5 receives data packets from the remote interface device 10. More specifically, the remote data node 5 receives data packets from the first-level data node 3. A remote feedback node 6 receives the input from the primary remote input node 5 and generates an additional output which is sent across the network 14 to the first-level feedback node 4 which can ultimately results in additional inputs used by the primary feedback node 2 to generate the output being used to control the feedback means 36. Thus, more sophisticated or specialized software at the remote location may be utilized for providing additional feedback to the biofeedback session. This also enables archived data and/or expert systems to be incorporated into the feedback session. In addition, data may be shared among a group of remote interface devices 10 to simulate a group session.

A second remote input node 7 receives data from the input node 5 in preparation of presenting the data at the remote location for monitoring by a session monitor 18. The second remote input node 7 extracts trend or other high level data from the remote input node 5. The second remote input node 7 may interact with a database containing normative data or rules and allow more detailed analysis of current performance of the biofeedback session. One output of the second remote input node 7 goes to the remote output means 40. The remote output means 40 communicates biofeedback session data to the session monitor 18. In addition to displaying charts and graphs of the various physiological data received by the input means 34, the remote output means 40 may display more specialized analysis generated by software at the remote interface device 20 such as trending. Furthermore, the remote output means 40 may include speakers for audio output or a video output enabling the session monitor 18 to listen, watch or otherwise observe the user 16. Furthermore, the remote output means 40 is capable of retrieving data from either the remote database 44 or local database 38.

The session monitor 18 may adjust the system parameters, and ultimately the feedback means 36 by utilizing the remote input means 42. Typically the remote input means 42 would comprise a keyboard and mouse connected to a computer which displays available or currently selected options. The remote input means 42 may also utilize video or audio inputs as well. The adjustments made by the session monitor 18 at the remote input means 42 is communicated to the secondary remote feedback node 8. The secondary remote node 8 in addition to receiving data input by the session monitor 18, integrates analysis and data received from the secondary remote input node 7, and produces an output. The output from the secondary remote feedback node 8 is sent to the primary remote feedback node 6 which controls the output of the primary remote feedback node 6. The output of remote feedback node 6 is then sent to the first-level feedback node 4, adjusting the output of the first-level feedback node 4 which is then sent to primary feedback node 2, adjusting the output of primary feedback node 2 which controls feedback means 36.

The operation of the system can be understood in terms of functional control loops. Each control loop has a particular set of response delay characteristics and corresponding data processing and manipulation characteristics. Loops with longer response times would have higher level or more sophisticated functions. Thus, a system which combines highly trained human professional personnel as well as high-level computer processing elements can be attained.

The first control loop, the primary local loop, the path shown as 46a, 46b and 46c, is comprised of the input means 34, the primary input node 1, the primary feedback node 2, the feedback means 36. This loop has a characteristic response time of 1 to 100 milliseconds. This loop has the ability to make simple determinations of signal parameters based upon analysis of input signal characteristics. While the parameters of this loop may be set by an adaptive system at a higher level, this loop would not include adaptive processing of its own.

The primary control loop by itself is a simple biofeedback loop. Physiological data from this loop are made available in a simple, direct manner so that the subject can become aware of them.

The secondary local loop, adds the nodes connected by 47a, 47b, and 47c to 46a and 46c. This loop receives input from the primary input node 1 and produces an output that is feedback into the primary feedback node 2. When only the primary control loop and secondary control loop are used, then a system of the type described in U.S. Pat. No. 5,899,867 is produced. This provides functions suitable for self-administration of biofeedback training.

This loop has a characteristic response time from 100 to 1000 milliseconds. It includes control methods that extract information from the input such as FFT, digital filtering, autoregressive, or related methods. The time delay introduced by these methods is based upon the requirement to analyze an epoch, or extended duration of the input signal, in order to generate the output information. Delays are encountered in various forms, including the need to process epochs in discrete "chunks," delays inherent in band-pass or low-pass filtering, time necessary to compute adaptive parameters such as percent time over-threshold and average power, etc. They are not introduced by any particular processing limitations on hardware platform. The delays are inherent in the calculations, and would be present even if the hardware were infinitely fast. Certain functions could introduce very long delays, on the order of one to ten seconds, such as adaptive thresholding methods that require such an extent of historical data in order to compute values.

The primary remote loop introduces the new elements along the path shown as 48*a*, 48*b*, and 48*c*. The complete path for this loop is 46*a*, 47*a*, 48*a*, 48*b*, 48*c*, 47*c*, 46*c*. The connections across 48*a* and 48*c* are across a network or other long distance communication. In the preferred embodiment, 48*a* and 48*c* would occur across the Internet, allowing a spatial separation of hundreds or thousands of miles if desired.

This loop introduces an additional layer of control, mediated by a privileged, or highly capable remote processor. Typical functions provided by this level would include access to archival or normative data, use of proprietary algorithms, application of specialized or costly software algorithms, and use of licensed material. The characteristic response times would be in the range of 100 to 1000 milliseconds, based upon a combination of factors which would consist primarily of communication delays between the local and remote processors and access and processing delays incurred within the remote processor.

With the addition of the primary remote loop to the primary local loop and secondary local loop, a system is created wherein a remote service provider can provide additional control and analysis of the biofeedback session. The additional control can be provided by the use of specific software, databases, and other operational facilities. It also provides the possibility of using archived data and/or expert systems, or of sharing data and/or feedback sessions. This loop also provides the capability to simulate a group situation using the communications network to facilitate the experience.

The secondary remote input loop includes the additional elements along the path of 49*a*, 50*a*, 50*b* and 49*c*. The entire path of this loop is 46*a*, 47*a*, 48*a*, 49*a*, 50*a*, 50*b*, 49*c*,48*c*, 47*c*, and 46*c*. This loop communicates with the remote output means 40 and the remote input means 42.

The addition of this loop gives the system the additional capability of allowing an expert user, such as a technician or therapist, to interact with the biofeedback session. The session monitor 18 will have access to comprehensive information derived from the local processor 10 including telemetry, video, audio, and processed versions thereof, an in informative and interactive display. With the introduction of this level of control, executive decisions are facilitated. These can include selection of protocols and methods, decision strategies for setting biofeedback and self-regulation parameters and characteristics, or provision of interventive activities such as voice interaction, setting thresholds, modification of the biofeedback system, or administration of therapeutic services such as electromedical, pharmaceutical, or aromatherapy.

The characteristic time delays of this control loop are on the order of time delays inherent in the human activity associated with the control and intervention. This will typically be between one and ten seconds, for typical use of remote controls. However, because this level of control incorporates a human professional as a component, delays of many days, months, or even years might be anticipated, as the system is able to provide extended, accurate, and updated therapeutic services to a subject over a long period of time and incorporates decisions and modifications that are based upon the entire extent of the subject's interaction with the system.

In the overall system, each control loop functions simultaneously with the others, providing an interactive set of concentric control systems. As a result, each level of control is maintained. While the outer levels exert a slower, modulating influence on the session, the short term processing capability is retained and operates in a stable, rapid manner. The longer term processing results are used to apply modulation, steering, configuration, and other slow, graded changes to the faster inner layers.

Figure 4:
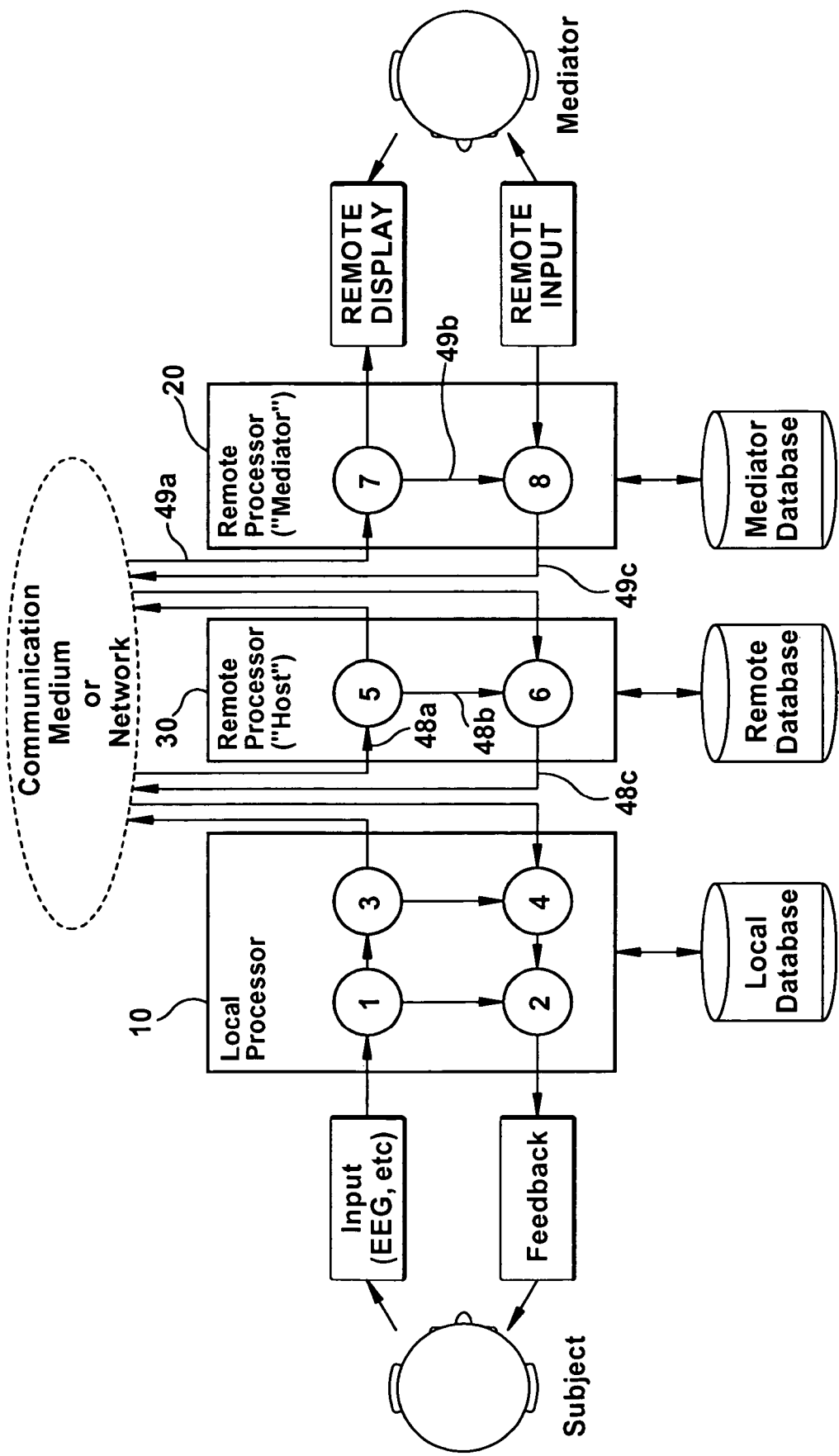
FIG. 4 is a detailed block diagram of the hardware components of an alternative embodiment of the present invention.

Referring to FIG. 4, more than one remote processor may be used, and this architecture may be extended accordingly. In FIG. 4 a secondary remote device 30 with an additional remote processor is added. Additionally, the secondary remote device 30 may have its own database 39.

The configuration of FIG. 4 offers even more flexibility. A service provider such as a health care network may utilize a plurality of secondary remote devices 30 to monitor biofeedback sessions automatically by computer while a plurality of session monitors 18 may monitor the sessions either randomly or by scheduled access. The secondary remote devices 30 may be utilized for software upgrades of the local processor 10 as well as provide long term monitoring for analysis after a session is completed and even keep records for billing. The remote database 44 serving as a mediator database can be utilized by the session monitor 18 to perform group or individual analysis which may occur during biofeedback sessions or at a later time.

With the addition of another processor and database, the configuration of FIG. 4 divides the secondary remote loop into two loops. In addition to the path previously described for the secondary remote loop, another loop is formed by the path 49*a*, 49*b* and 49*c*. Because this loop has separate processing and database capabilities, it is capable of operating independently of the primary remote control loop. In this embodiment, the secondary remote input node 7 would receive data, process the data independent of the primary remote input node 5, and through path 49*c* communicate and adjust the feedback from the secondary remote feedback node 8. Thus, remote feedback node 8 may generate an output based on either the secondary remote input node 7, the session monitor 18, or both.

The configuration as shown in FIG. 4 also enables the session monitor 18 to work independently of the secondary remote device 30. The communications network 14 can deliver data packets from the first-level input node 3 simultaneously to the primary remote input node 5 and the secondary remote input input node 7. In addition, the secondary remote node 7 may also receive data from the primary remote node 5 across the network 14. Additionally, the primary remote input node 5 may receive data from the secondary remote node 7. Similarly, this configuration also enables the first-level feedback node 4 to receive input from either the primary remote feedback node 6 or the secondary remote feedback node 8 independently.

Although the invention has been shown and described with respect to a certain preferred embodiment, it is obvious that equivalent alterations and modifications will occur to others skilled in the art upon the reading and understanding of this specification. The present invention includes all such equivalent alterations and modifications and is limited only by the scope of the following claims.

What is claimed is:

1. A distributed biofeedback system for managing a biofeedback session, comprising;
    (a) an input means for receiving physiological data from a user;
    (b) an output means for communicating feedback to the user;
    (c) an input node connected to the input means for receiving data from the input means;
    (d) a first-level data node connected to the input node for receiving and processing data received from the input node;
    (e) a remote input node connected to the first-level data node for receiving data from the first-level data node and further processing the data and preparation of the data for remote outputting;
    (f) a remote feedback node having remote feedback inputs connected to the remote input node for producing a remote feedback output responsive to the remote feedback inputs;
    (g) a first-level feedback node having first-level feedback inputs connected to the first-level data node and the remote feedback node for producing a first-level feedback output responsive to the first-level feedback inputs;
    (j) a primary feedback node having primary feedback inputs connected to the input node and the first-level feedback node for producing a primary feedback output for controlling the output means.

2. The distributed biofeedback system for managing a biofeedback session as in claim 1, further comprising a local database for storing and retrieving data from a local node, a first-level input node, a first-level feedback node, and a primary feedback node.

3. The distributed biofeedback system for managing a biofeedback session as in claim 2, further comprising a remote database for storing and retrieving data from the remote input node and remote feedback node.

4. The distributed biofeedback system for managing a biofeedback session as in claim 3, further comprising remote output means connected to a second remote input node for communicating data to a monitor at a remote location; and remote input means for receiving input from the monitor at the remote location.

5. The distributed biofeedback system for managing a biofeedback session as in claim 1, further comprising:
    (a) a second remote input node connected to the remote input node for receiving data from the remote input node and further processing the data and preparation of the data for remote outputting;
    (b) remote output means connected to the second remote input node for communicating data to a monitor at a remote location;
    (c) remote input means for receiving input from the monitor at the remote location;
    (d) a second remote feedback node having secondary remote feedback inputs connected to the remote input means and second remote input node for producing a second remote feedback output responsive to the secondary remote feedback inputs, the second remote feedback node being connected to one of the inputs of the remote feedback node.

6. The distributed biofeedback system for managing a biofeedback session as in claim 2, wherein the remote input node is connected to a first-level data node by the Internet and the remote feedback node is connected to the first-level feedback node by the Internet.

7. The distributed biofeedback system for managing a biofeedback session as in claim 2, wherein the second remote input node is connected to the remote node by the Internet and the output of the second remote feedback node is connected to the input of the remote feedback node by the Internet.

8. The distributed biofeedback system for managing a biofeedback session as in claim 7, further comprising:
    (a) a local database for storage and retrieval of data input into the input node and the first-level data node, and data output from the primary feedback node and the first-level feedback node;
    (b) a first remote database for storage and retrieval of data input into the remote input node, and data output from the remote feedback node;
    (c) a second remote database for storage and retrieval of data input into the second remote input node, and data output from the second remote feedback node.

9. The distributed biofeedback system for managing a biofeedback session as in claim 2, further comprising computer readable instructions on a computer readable medium having instructions for selecting and outputting data from the local database to the remote output means; and computer readable instructions for selecting and outputting data from the first remote database to the remote output means; and computer readable instructions for selecting and outputting data from the second remote database to the output means.

10. The distributed biofeedback system for managing a biofeedback session as in claim 9, further comprising computer readable instructions for controlling the output of the primary feedback node from the remote input means; computer readable instructions for controlling the output of the remote feedback node from the remote input means, and;
    computer readable instructions for controlling the output of the second remote feedback node from the remote input means.

* * * * *